Figure 1A:
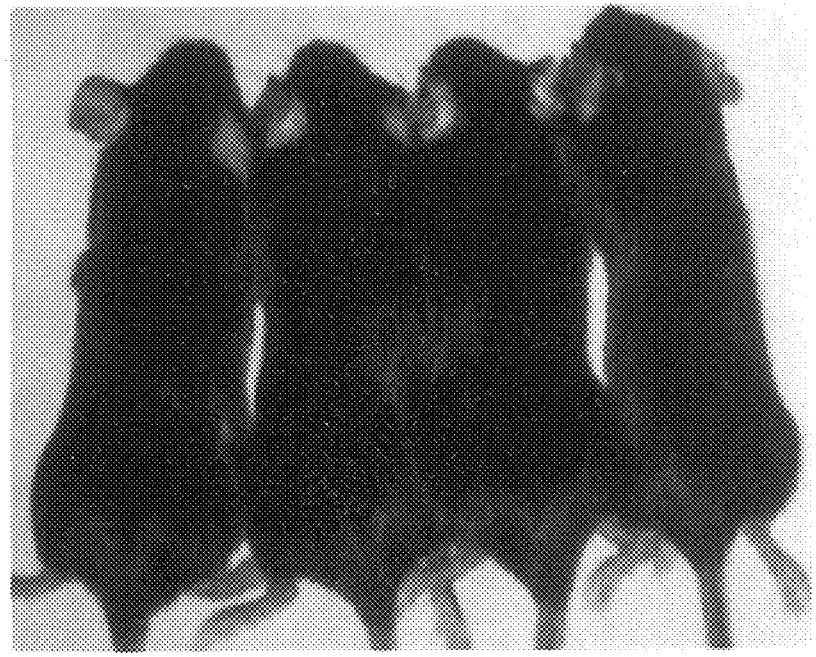

United States Patent [19]
Moran et al.

[11] Patent Number: 5,962,523
[45] Date of Patent: Oct. 5, 1999

[54] METHODS OF USING BUTYRIC ACID DERIVATIVES TO PROTECT AGAINST HAIR LOSS

[75] Inventors: S. Mark Moran, Orinda; Thomas R. Alessi, Hayward, both of Calif.

[73] Assignee: Discovery Laboratories, Inc., Doylestown, Pa.

[21] Appl. No.: 08/738,167

[22] Filed: Oct. 25, 1996

[51] Int. Cl.⁶ .................................................. A61K 31/225
[52] U.S. Cl. .......................... 514/547; 514/557; 514/561; 514/880
[58] Field of Search .................... 514/547, 557, 514/561

[56] References Cited

U.S. PATENT DOCUMENTS 5,200,553  4/1993  Nudelman et al. ..................... 560/263

OTHER PUBLICATIONS

CA 117:198227, Contier et al, 1992.
CA 115:189778, Hasunuma et al, 1991.
CA 116:91158, Schmidt—Aebert, 1992.
CA 118: 240479, 1993.
CA 123:122719, Hasunuma, 1995.
CA 123:17469, Hasunuma, 1995.
CA 123:179085, Behzadi et al, 1995.
CA 125:123227, Vasiliev, Jun. 1996.

*Primary Examiner*—Rebecca Cook
*Attorney, Agent, or Firm*—Pennie & Edmonds LLP

[57] ABSTRACT

The present invention relates to methods of protecting against injury to hair follicles in a mammal by administering an effective amount of butyric acid or a biologically active butyric acid derivative. In particular, this invention relates to the use of cell differentiation-inducing butyric acid derivatives to protect against hair loss in cancer patients undergoing chemotherapy and/or radiation therapy.

18 Claims, 6 Drawing Sheets

METHODS OF USING BUTYRIC ACID DERIVATIVES TO PROTECT AGAINST HAIR LOSS

1. INTRODUCTION

The present invention relates to methods of protecting against injury to hair follicles in a mammal by administering an effective amount of butyric acid or one or more of its biologically active derivatives. In particular, this invention relates to the use of butyric acid derivatives to protect against hair loss or damage in human cancer patients undergoing chemotherapy and/or radiation therapy.

2. BACKGROUND OF THE INVENTION

Alopecia (hair loss) is a common condition that results from diverse causes. In particular, alopecia frequently occurs in cancer patients who are treated with chemotherapeutic drugs such as cyclophosphamide (CY) and/or irradiation. Such agents damage hair follicles which contain mitotically active hair-producing cells. Such damage may cause abnormally slow growth of the hair or may lead to frank loss. While various attempts have been made to protect against alopecia or abnormal rates of hair growth during such treatments, there remains a need for an agent that prevents damage to hair follicles in a safe and effective manner.

U.S. Pat. No. 5,200,553 (issued Apr. 6, 1993) describes a class of compounds referred to as carboxylic acid esters that promote antitumor or immune responses. These compounds are believed to be capable of penetrating the membranes of cells and undergoing hydrolytic cleavage intracellularly to result in butyric acid, which can induce cell differentiation and displays antineoplastic activity.

The same class of compounds has also been shown to increase fetal hemoglobin levels in red blood cells and thus are useful for the treatment of β-globin disorders such as sickle cell anemia and thalassemia (WO 95/24189, published Sep. 14, 1995). In addition, butyrate and α-amino-n-butyric acid have been used to stimulate the expression of fetal globin gene (Perrine et al., 1993, *N. Eng. J. Med.* 328:81; Perrine et al., 1989, *Blood* 74:454).

However, none of the aforementioned references discloses other activities of butyric acid or butyric acid derivatives, and in particular, the ability to protect against hair damage or loss in a mammal as described herein.

3. SUMMARY OF THE INVENTION

The present invention relates to methods for protecting against injury to hair follicles in a mammal by administering one or more compounds encompassed by the following structure:

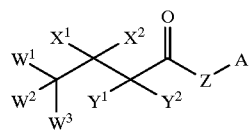

wherein:

$W^1$, $W^2$ and $W^3$ each independent from the other represents H, F, Br, Cl, I, aryl, $OR^1$, $NR^1R^2$ or $W^1$ and $W^2$ taken together represent a carbonyl group (=O);

$X^1$ and $X^2$ each independent from the other represents H, F, Br, Cl, I, methyl, $CF_3$, aryl, $OR^1$, $CH_2R^1$, $NR^1R^2$ or $X^1$ and $X^2$ taken together represent a carbonyl group (=O);

$Y^1$ and $Y^2$ each independent from the other represents H, F, Br, Cl, I, methyl, $CF_3$, ethyl, perfluoroethyl, aryl, $OR^1$, $CH_2OR^1$, $CH_2CH_2OR^1$, $CHOR^1CH_3$, $NR^1R^2$ or $Y^1$ and $Y^2$ taken together represent a carbonyl group (=O);

where $R^1$ and $R^2$ each independent from the other represents H, $C_1$–$C_7$ alkyl, aryl, arylalkyl or C(=O)$CH_2CH_2CH_3$;

Z represents O or $NR^3$ where $R^3$ is H, alkyl, aryl or arylalkyl; and

A represents H, alkyl, aryl, arylalkyl, carbocyclic, Q—$CHR^4$—O—C(=O)$R^5$ or $CHR^4$—O—C(=O)—O—$R^5$ where Q represents a covalent bond, alkyl, or substituted alkyl where one or more substituents is —OC(=O)$R^5$;

$R^4$ represents H, alkyl, aryl, arylalkyl; and $R^5$ represents alkyl, aminoalkyl,

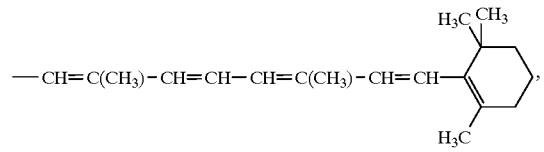

arylalkyl or aryl, in which aryl by itself, and aryl in arylalkyl are each selected from the group consisting of phenyl, naphthyl, furyl, or thienyl, each of which is unsubstituted or substituted by at least one substituent selected from the group consisting of alkyl, alkoxy and halogen.

The methods of the present invention also include pharmaceutically acceptable salts and prodrugs of the aforementioned structures.

The present invention is based, in part, on Applicants' discovery that in an animal model, while chemotherapy causes hair loss and/or impedes hair growth, such effects are prevented or mitigated by topical administration of butyric acid derivatives to the skin. Therefore, a method is provided for protecting against hair loss or impeded hair growth in an individual undergoing chemotherapy and/or radiation therapy. In this connection, while it is possible to utilize the compounds in vivo as raw chemicals, it is preferable to administer them as a pharmaceutical composition which contains butyric acid or a butyric acid derivative as an active ingredient.

4. BRIEF DESCRIPTION OF THE DRAWINGS

Figure 1B:
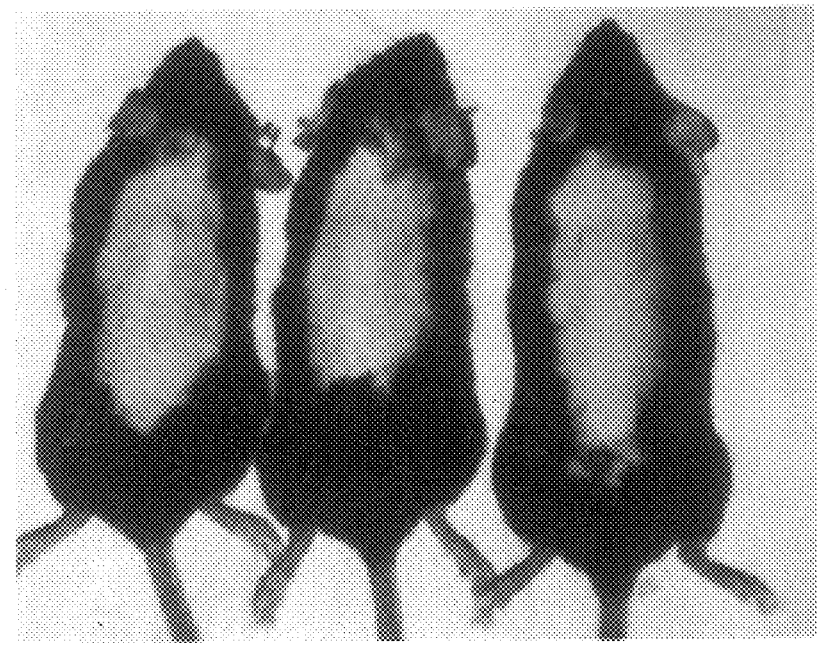

FIG. 1A and 1B. Demonstration of hair removal from normal mice (1A) by depilation (1B) on day 0 of the experiment. The back of each animal was wax-stripped to remove the hair prior to further treatments in order to make more visible the changes effected by the treatments.

Figure 2:
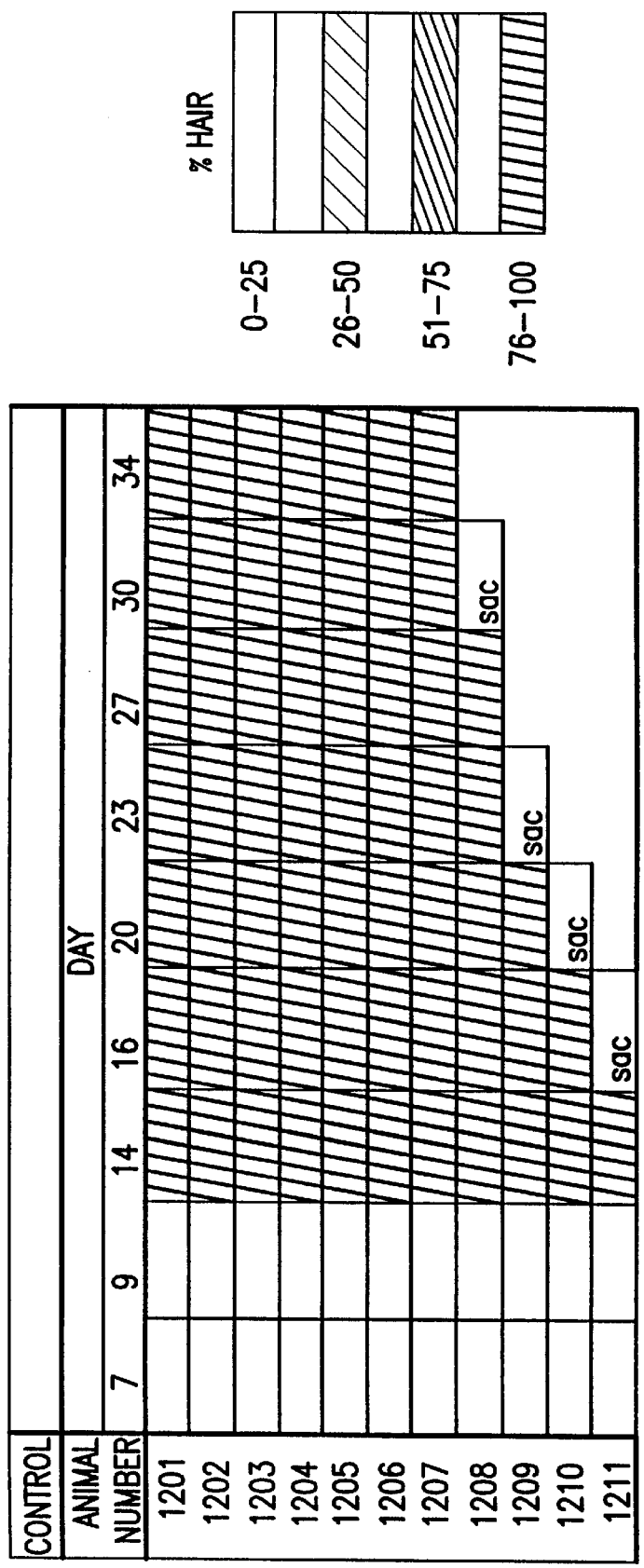

FIG. 2. By day 14, all mice in the control group had complete hair regrowth. The term "Sac" refers to "sacrifice" of certain animals for histological examination of the hair follicles.

Figure 3:
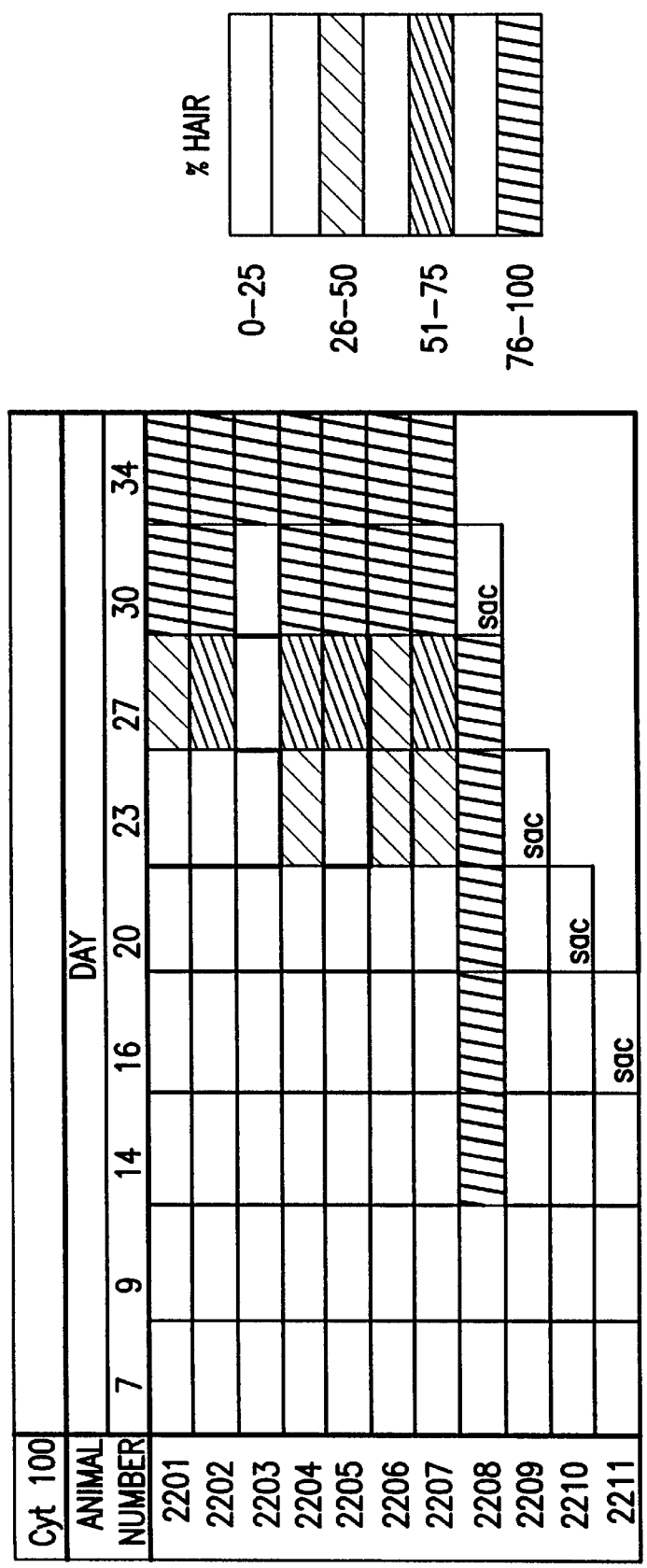

FIG. 3. When the wax-stripped animals began to regrow their hair, the animals in the CY group, treated with CY alone 9 days after depilation, displayed a substantial delay in hair regrowth as compared to untreated control animals shown in FIG. 2, indicating that CY caused injury to hair follicles. The term "Sac" refers to "sacrifice" of certain animals for histological examination of the hair follicles.

Figure 4:
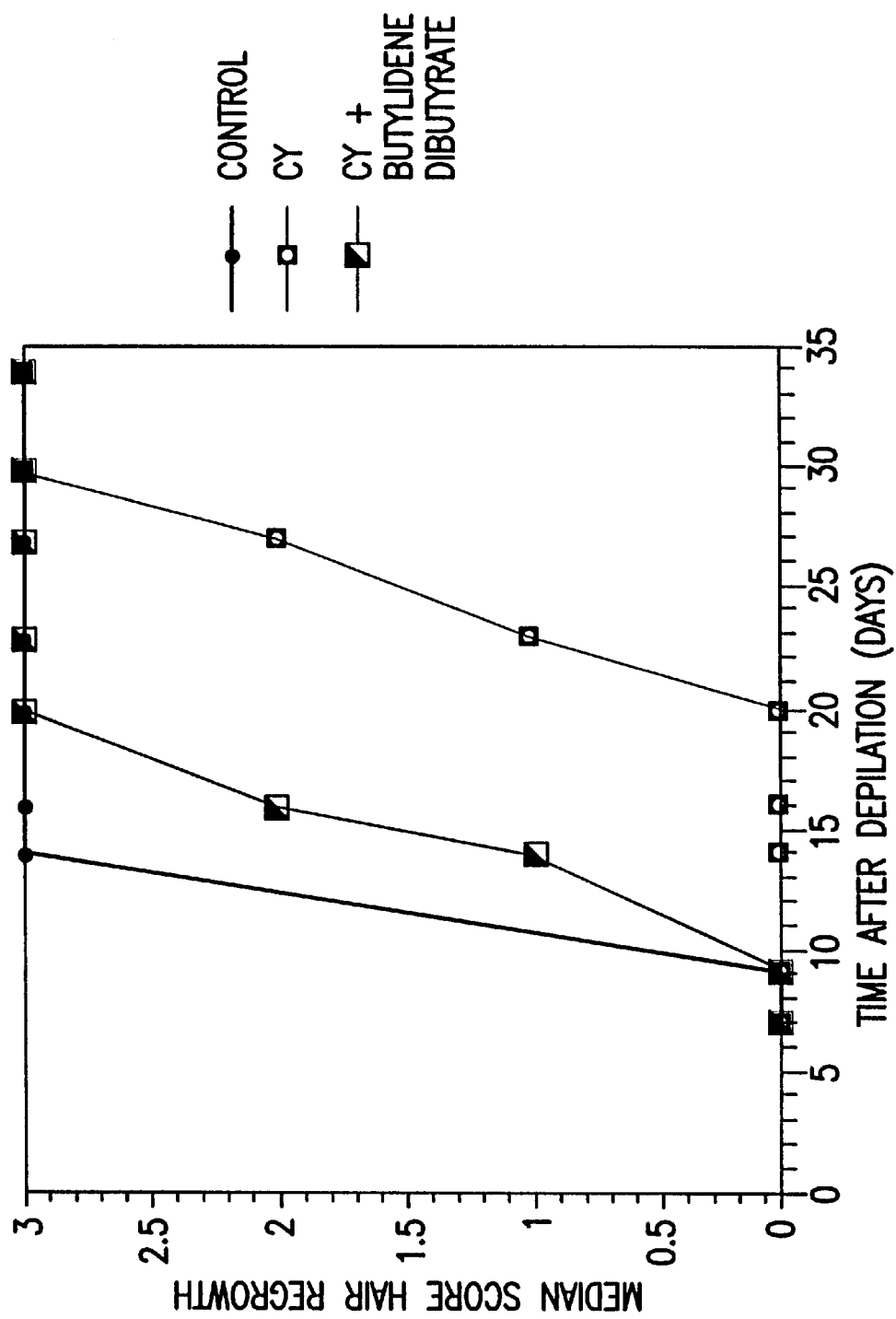

FIG. 4. Animals treated with both CY and butylidene dibutyrate showed accelerated hair regrowth as compared to those animals undergoing CY treatment alone, indicating the ability of a butyric acid derivative to protect against injury to hair follicles.

Figure 5:
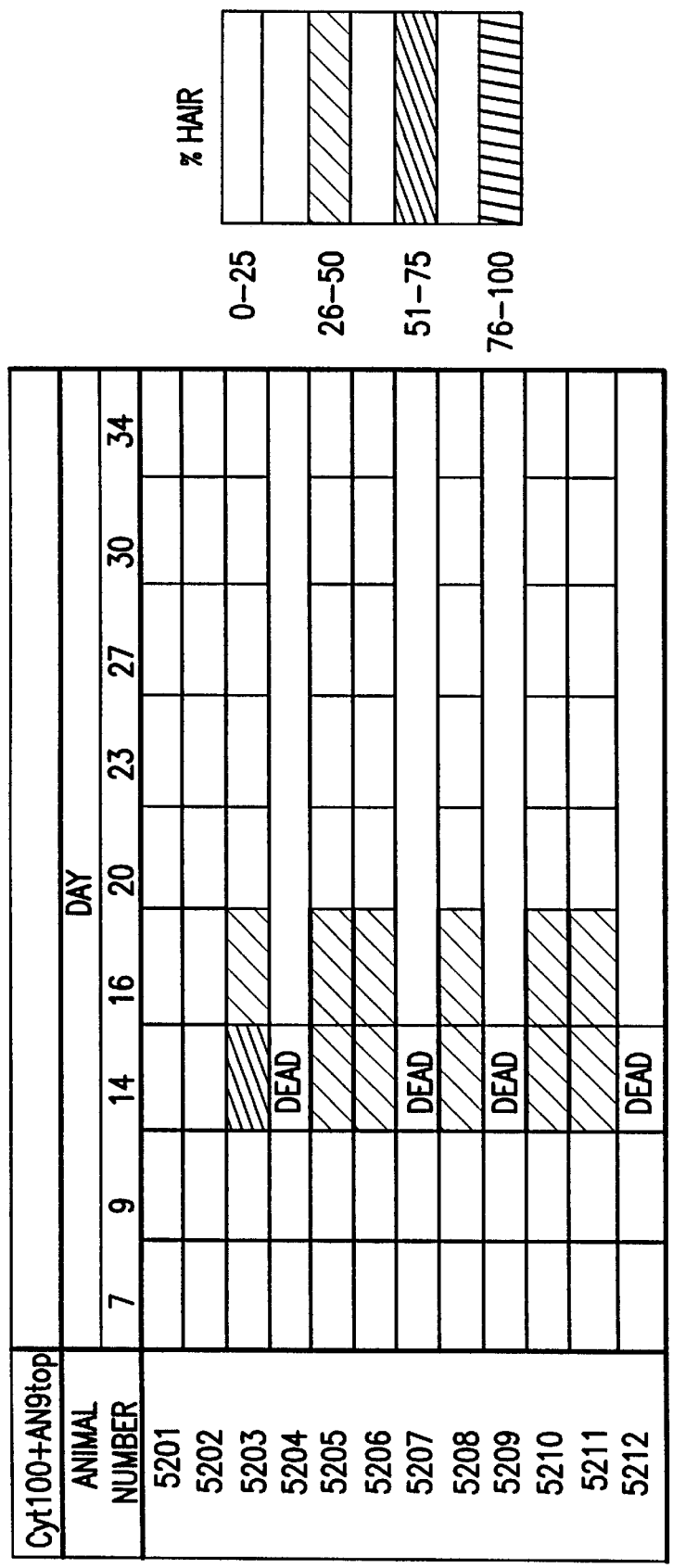

FIG. 5. Animals treated with both CY and pivaloyloxymethyl butyrate also showed accelerated hair regrowth as compared to CY treatment alone, indicating the ability of a butyric acid derivative to protect against injury to hair follicles.

Figure 6A:
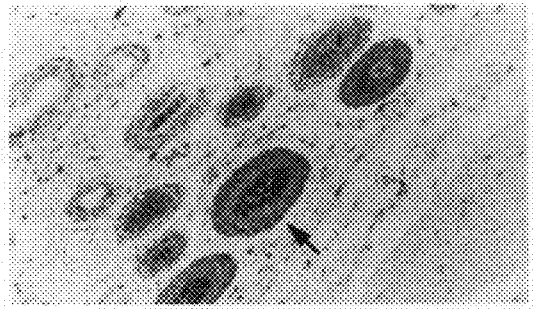
Figure 6B:
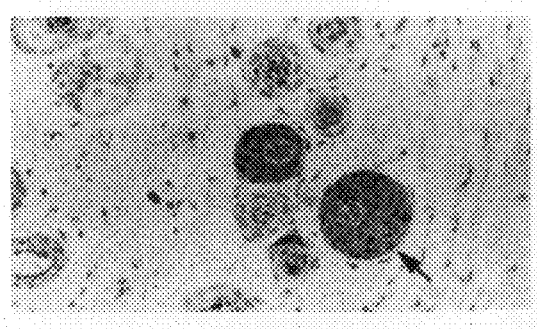
Figure 6C:
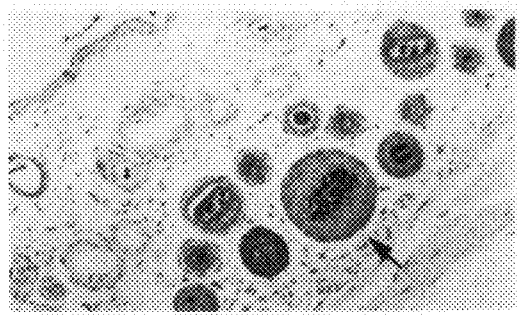

FIG. 6A–6C. Histological examination of the skin of animals on day 14 in the control group (6A), CY-treated group (6B) and CY plus butylidene dibutyrate-treated group (6C) confirmed the visual observations as shown in FIGS. 2, 3 and 4. While the hair follicles (arrow) in the skin of the control animals displayed normal morphology, the CY-treated follicles lost the hair pigment in their center and manifested abnormal cellular architecture. However, the hair follicles of animals treated with CY and a butyric acid derivative more closely resemble the normal follicles than those treated with CY alone.

5. DETAILED DESCRIPTION OF THE INVENTION

The present invention relates to methods of using butyric acid or butyric acid derivatives to protect against injury to hair follicles. The invention is discussed in more detail in the subsections below, solely for the purpose of description and not by way of limitation. For clarity of discussion, the specific procedures and methods described herein are exemplified using a murine model. These procedures and methods are merely illustrative for the practice of the invention. Analogous procedures and techniques, as well as other compounds, are equally applicable to mammals, including humans.

5.1 Butyric Acid and its Derivatives

The present invention provides a method for protecting against injury to hair follicles as manifested by hair loss or slow rates of hair regrowth in a subject in need of chemotherapy and/or radiation treatment by administering one or more compounds encompassed by the structure of:

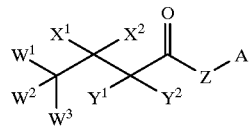

wherein:

$W^1$, $W^2$ and $W^3$ each independent from the other represents H, F, Br, Cl, I, aryl, $OR^1$, $NR^1R^2$ or $W^1$ and $W^2$ taken together represent a carbonyl group (=O);

$X^1$ and $X^2$ each independent from the other represents H, F, Br, Cl, I, methyl, $CF_3$, aryl, $OR^1$, $CH_2OR^1$, $NR^1R^2$ or $X^1$ and $X^2$ taken together represent a carbonyl group (=O);

$Y^1$ and $Y^2$ each independent from the other represents H, F, Br, Cl, I, methyl, $CF_3$, ethyl, perfluoroethyl, aryl, $OR^1$, $CH_2OR^1$, $CH_2CH_2OR^1$, $CHOR^1CH_3$, $NR^1R^2$ or $Y^1$ and $Y^2$ taken together represent a carbonyl group (=O);

where $R^1$ and $R^2$ each independent from the other represents H, $C_1$–$C_7$ alkyl, aryl, arylalkyl or C(=O) $CH_2CH_2CH_3$;

Z represents O or $NR^3$ where $R^3$ is H, alkyl, aryl, arylalkyl; and

A represents H, alkyl, aryl, arylalkyl, carbocyclic, Q—$CHR^4$—O—C(=O)$R^5$ or $CHR^4$—O—C(=O)—O—$R^5$ where Q represents a covalent bond, alkyl, or substituted alkyl where one or more substituents is —OC(=O)$R^5$;

$R^4$ represents H, alkyl, aryl, arylalkyl; and $R^5$ represents alkyl, aminoalkyl,

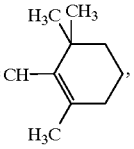

arylalkyl or aryl, in which aryl by itself, and aryl in arylalkyl are each selected from the group consisting of phenyl, naphthyl, furyl, or thienyl, each of which is unsubstituted or substituted by at least one substituent selected from the group consisting of alkyl, alkoxy and halogen.

The methods of the invention also include pharmaceutically acceptable salts and prodrugs of butyric acid and butyric acid derivatives encompassed by the above structure.

For the compounds encompassed by the methods of the invention and for the pharmaceutical compositions which contain such compounds, it is preferred that alkyl radicals, including those which form part of alkoxy and arylalkyl radicals contain no more than about 30 carbon atoms.

A preferred method of the present invention comprises the administration of a compound encompassed by the aforementioned structure wherein $W^1$ is H, F, $OR^1$, phenyl, substituted phenyl or $NR^1R^2$; $X^1$ is H, F, $OR^1$, methyl, $CF_3$, $CH_2OR^1$, phenyl, substituted phenyl or $NR^1R^2$; $Y^1$ is H, F, $OR^1$, methyl, $CF_3$, $CH_2OR^1$, phenyl, substituted phenyl, ethyl, perfluoroethyl, $CH_2CH_2OR^1$, $CHOR^1CH_3$ or $NR^1R^2$; $W^2$, $W^3$, $X^2$ and $Y^2$ are H or F; where $R^1$ and $R^2$ are H, $C_1$–$C_5$ alkyl, phenyl, substituted phenyl or C(=O) $CH_2CH_2CH_3$; Z is O or $NR^3$ where $R^3$ is H, alkyl, aryl, arylalkyl; and A is H, alkyl, aryl, arylalkyl, carbocyclic, Q—$CHR^4$—O—C(=O)$R^5$ or $CHR^4$—O—C(=O)—$OR^5$ where Q is a covalent bond, alkyl or substituted alkyl where one or more substituents is —OC(=O)$CH_2CH_2CH_3$. $R^4$ represents H, alkyl, aryl, arylalkyl and $R^5$ represents $C_1$–$C_7$ alkyl,

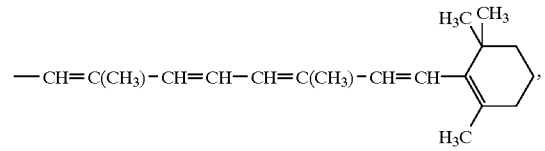

arylalkyl or aryl, in which aryl by itself, and aryl in arylalkyl are each selected from the group consisting of phenyl, naphthyl, furyl, or thienyl, each of which is unsubstituted or substituted by at least one substituent selected from the group consisting of alkyl, alkoxy and halogen.

Specifically preferred is the method which comprises the administration of a compound encompassed by the aforementioned structure wherein $W^1$ is H, F, phenyl, $NH_2$, $OR^1$; $X^1$ is H, F, methyl, $CF_3$, $OR^1$, $CH_2OR^1$, phenyl or $NH_2$; $Y^1$ is H, F, methyl, $CF_3$, $OR^1$, $CH_2OR^1$, ethyl, perfluoroethyl, phenyl, $CH_2CH_2OR^1$, $CHOR^1CH_3$ or $NH_2$ where $R^1$ is H, $C_1$–$C_5$ alkyl or C(=O)$CH_2CH_2CH_3$; $W^2$, $W^3$, $X^2$ and $Y^2$ are H or F; Z is O or NH; and A is H, alkyl, aryl, arylalkyl, carbocyclic, Q—$CHR^4$—O—C(=O)$R^5$ or $CHR^4$—O—C(=O)—O—$R^5$ where Q is a covalent bond, alkyl or substituted alkyl where one or more substituents is —OC(=O)CH$_2$CH$_2$CH$_3$; R$^4$ is H, C$_1$–C$_7$ alkyl; and Rs is C$_1$–C$_7$ alkyl or

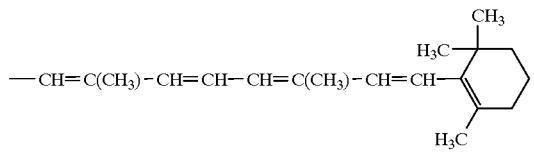

More specifically preferred is the method which comprises the administration of a compound encompassed by the aforementioned structure wherein W$^1$, W$^2$, W$^3$, X$^1$, X$^2$, Y$^1$ and Y$^2$ are H; Z is O or NH; and A is H, alkyl, aryl, arylalkyl, carbocyclic, Q—CHR$^4$—O—C(=O)R$^5$ or CHR$^4$—O—C(=O)—O—R$^5$ where Q is a covalent bond, C$_1$–C$_5$ alkyl or substituted C$_1$–C$_5$ alkyl where one or more substituents is —OC(=O)CH$_2$CH$_2$CH$_3$; R$^4$ is H or C$_1$–C$_5$ alkyl; and R$^5$ is C$_1$–C$_7$ alkyl or all trans

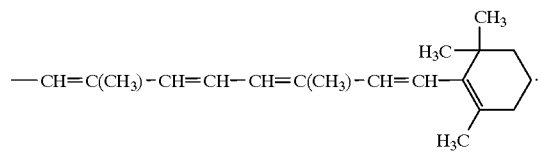

Examples of such a compound include, but are not limited to, butyric acid, butyrate salts, butyramides, butyric acid esters and isomers thereof. In particular, a butyric acid ester is selected from the group consisting of butylidene dibutyrate; pivaloyloxymethyl butyrate; ethylidene dibutyrate; (1-butyroyloxy)ethyl ethyl carbonate; 2,2-dimethylpropylidene dibutyrate; 3-(butyroyloxy)phthalide; (butyroyloxy)methyl octanoate; methylidene dibutyrate; ((2-methylpropanoyl)oxy)methyl butyrate; tocopheryl butyrate; glyceryl tributyrate; and retinoyloxymethyl butyrate.

The compounds suitable for use in the methods herein described may have asymmetric centers. All chiral, diastereomeric, and racemic forms are included in the present invention. Many geometric isomers of olefins and the like can also be present in the compounds described herein, and all such stable isomers are encompassed in the present invention.

When any variable (for example, R$^1$, R$^2$, R$^3$, R$^4$ and R$^5$ etc.) occurs more than one time in any constituent or in the structure described above or any other formula herein, its definition on each occurrence is independent of its definition at every other occurrence. Also, combinations of substituents and/or variables are permissible only if such combinations result in stable compounds.

For the purpose of this application, "alkyl" is intended to include both branched-, straight- or cyclic-saturated aliphatic hydrocarbon groups having the specified number of carbon atoms; e.g. methyl, ethyl, propyl, isopropyl, butyl, isobutyl, secondary butyl, tertiary butyl, hexyl, cyclohexyl, heptyl, octyl, decyl, dodecyl or octadecyl. As used herein and in the claims, "aryl" or "aromatic residue" is intended to mean phenyl, furyl, thienyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin). Aryl radicals, including those which form part of arylalkyl, aryloxy and aralkoxy radicals, may be substituted or not, and may be carbocyclic; substituents when present may be selected from, e.g. alkyl, alkoxy and halogen. The term "alkoxy", as used herein and in the claims, represents an alkyl group of indicated number of carbon atoms attached through an oxygen bridge.

The term "substituted", as used herein and in the claims, means that one or more hydrogens on the designated atom is replaced with a selection from the indicated group, provided that the designated atom's normal valency is not exceeded, and that the substitution results in a stable compound. By "stable compound" or "stable structure" is meant herein a compound that is sufficiently robust to survive isolation to a useful degree of purity from a reaction mixture, and formulation into an efficacious therapeutic agent.

As used herein and in the claims, "therapeutically effective amount" refers to that amount necessary to administer to a host to achieve the desired result of protection against injury to hair follicles.

As used herein and in the claims, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo in relation to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

5.2 Preparation of Butyric Acid Derivatives

The compounds of the present invention may be prepared generally by any method known in the art. For the formation of an ester group or a carbonate group, the method described in U.S. Pat. No. 5,200,533 may be used.

For example, compounds wherein R$^5$ is other than propyl may be prepared by reacting butyric acid with a reagent of formula Y—CHR$^4$—O—(O=)C—R$^5$ in the presence of a base, where Y is leaving group such as halogen, methanesulfonate or P-toluenesulfonate, and R$^4$ and R$^5$ are as previously defined. The base may be, e.g., a trialkylamine, pyridine or an alkali metal carbonate. The reaction may be carried out in the absence or presence of an inert solvent. When a solvent is used, this may be, for example, acetone, ether, benzene, toluene, tetrahydrofuran, ethyl acetate, acetonitrile, dimethylformamide, dimethyl sulfoxide, chloroform, dioxane or 1,2-dichloroethane.

When R$^5$ is propyl, the compounds may be prepared by an alternate process by reacting butyric anhydride with an aldehyde of the formula (R$^4$—CHO), wherein R$^4$ is as defined above, in the presence of an acid catalyst such as boron trichloride, aluminum trichloride, tin dichloride, sulfuric acid, phosphoric acid or zinc chloride.

Several compounds suitable for use in the present invention are illustrated by the following non-limiting examples:

5.2.1 Butylidene Dibutyrate

To ice-cooled $BF_3$-etherate (8.66 g., 61 mmol.) is added dropwise via a syringe, over one hour, a mixture of butyric anhydride (6.58 g., 41.6 mmol.) and butyraldehyde (1.22 g., 27.7 mmol.). The reaction mixture is stirred for an additional 2 hours, 10% aq. sodium acetate solution (28 ml.) is added, and the mixture again stirred for 45 minutes. The oily layer is extracted into ether (2×25 ml.), and the combined ethereal extracts are washed with saturated aqueous sodium bicarbonate solution until no further evolution of $CO_2$ is observed. The organic phase is then washed with water, dried over magnesium sulfate, filtered, concentrated and the residue is fractionally distilled at 8–12 mm. $^1$H-NMR ppm ($CDCl_3$): 6.82 (t, J=5.6 Hz, 1H), 2.30 (m, 4H), 1.75 (m, 2H). 1.65 (sextet, J=7.5 Hz, 4H), 1.40 (q, J=7.5 Hz, 2H). 0.953 and 0.949 (2t, J=7.5 Hz, 9H).

5.2.2 Pivaloyloxymethyl Butyrate

To a mixture of butyric acid (5.7 ml., 40 mmol.) and chloromethyl pivalate (18 ml., 1 mmol.) in acetone (10 ml.) is added triethylamine (12.17 ml., 88 mmol.). The reaction mixture is stirred at room temperature for 24 hours, it is then evaporated and the residue is treated with a mixture of water and ethyl acetate. The organic phase is separated, dried over potassium carbonate, filtered and evaporated. The residue is fractionally distilled, to give the title compound (4.42 g., yield 57%). b.p. 88°–93° C./2 mm. $^1$H-NMR ppm ($CDCl_3$): 5.753 (s, 2H). 2.336 (t, 2H), 1.670 (sextet, 2H), 1.213 (s. 9H). 0.953 (t, 3H).

5.2.3 Ethylidene Dibutyrate $^1$H H-NMR ppm ($CDCl_3$); 6.88 (q. J=5.6 Hz, 1H), 2.30 dt, J=0.75, 7.5 Hz, 4H), 1.65 (sextet, J=7.5 Hz. 4H). 1.47 (d. J=5.5 Hz, 3H). 0.95 (t, J=7.5 Hz, 6H).

5.2.4 (1-Butyroyloxy)Ethyl Ethyl Carbonate $^1$H-NMR ppm ($CDCl_3$): 6.77 (q. J=5 Hz, 1H), 4.22 (q. J=7 Hz, 2H), 2.32 (t, J=7.5 Hz, 2H), 1.66 (sextet, J=7.5 Hz, 2H), 1.52 (d, J=5.5 Hz, 3H), 1.318 (t, J=7.5 Hz, 3H), 0.95 (t, J=7.5 Hz, 3H).

5.2.5 2,2-Dimethylpropylidene Dibutyrate $^1$H-NMR ppm ($CDCl_3$): 6.59 (s, 1H), 2.31 (t, 4H), 2.20 (sextet, 4H), 1.50 (s, 9H), 1.49 (t, 6H).

5.2.6 Octanoyloxymethyl Butyrate $^1$H-NMR ppm ($CDCl_3$): 5.70 (s, 2H), 2.38–2.11 (m, 4H), 1.7–1.6 (m, 4H), 1.3–1.1 (m, 8H), 0.92 (t, 3H), 0.87 (t, 3H).

5.2.7 3-(Butyroyloxy)Phthalide $^1$H-NMR ppm ($CDCl_3$): 7.93 (dd, J=0.7, 7.5 Hz, 1H), 7.76 (dt, J=1.1, 7.5 Hz, 1H), 7.65 (dt, J=1.0, 8.2 Hz, 1H), 7.58 (dd, J=0.7, 8.2 Hz, 1H), 7.46 (s, 1H), 2.42 (t, J=7.4, Hz, 2H), 1.72 (sextet, J=7.4, Hz, 2H), 0.99 (t, J=7.4, Hz, 3H).

5.2.8 Iso-Butyroyloxymethyl Butyrate $^1$H-NMR ppm ($CDCl_3$): 5.77 (s, 2H), 2.60 (septet, 1H), 2.36 (t, 2H), 1.69 (sextet, 2H), 1.19 (d, 6H), 0.96 (t,3H).

The procedures outlined above can be improved by one skilled in the art by, for instance, changing the temperature or stoichiometry of the reactions. Any such changes are intended to fall within the scope of this invention.

5.3 Dosage and Formulation

The compounds described in Sections 5.1 and 5.2 supra, may be administered for the protection against injury to hair follicles by any means that produces contact of the active agent with the agent's site of action in the body of a mammal. They can be administered by any conventional means available for use in conjunction with pharmaceuticals, either as individual therapeutic agents or in a combination of therapeutic agents. Each can be administered alone but is generally administered with a pharmaceutical carrier selected on the basis of the chosen route of administration and standard pharmaceutical practice. The pharmaceutical compositions of the invention may be adapted for oral, parenteral, topical or rectal administration, and may be in unit dosage form, in a manner well known to those skilled in the pharmaceutical art. Parenteral administration includes but is not limited to, injection subcutaneously, intravenously, intraperitoneally or intramuscularly.

With respect to the timing of an injury to the hair follicle by chemotherapy and/or radiation therapy, treatment with the active ingredient may begin before, during or after the injurious event has occurred, with the preferred timing being from 3 to 7 days before chemotherapy and/or radiation therapy and continuing until 3 to 7 days after chemotherapy and/or radiation therapy has been completed.

The dose administered will, of course, vary depending upon known factors, such as: the pharmacodynamic characteristics of the particular agent and its mode and route of administration; the age, health, height and weight of the recipient; the nature and extent of the symptoms; the kind of concurrent treatment(s); the frequency of treatment(s); and the effect desired. A daily dose of active ingredient can be expected to be about 0.05 to 50 grams per kilogram of body weight, with the preferred dose being 1 to 10 grams per kilogram of body weight. When the active ingredient is administered topically to the skin (such as the scalp), the daily dose of active ingredient can be expected to be about 0.1 to 200 milligrams per square centimeter of surface area, with the preferred dose being 3.22 to 32.2 milligrams per square centimeter of surface area.

Dosage forms (compositions suitable for administration) contain from about 1 milligram to about 500 milligrams of active ingredient per unit. In these pharmaceutical compositions, the active ingredient is ordinarily present in an amount of about 0.5–95% by weight based on the total weight of the composition.

The active ingredient can be administered orally in solid or semi-solid dosage forms, such as hard or soft-gelatin capsules, tablets, or powders, or in liquid dosage forms, such as elixirs, syrups, or suspensions. It can also be administered parenterally, in sterile liquid dosage forms. Other dosage forms are potentially possible such as patches or ointment or transdermal administration.

Gelatin capsules or liquid-filled soft gelatin capsules may contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective disintegration in the gastrointestinal tract. Liquid dosage forms for oral administration can contain coloring and/or flavoring to increase patient acceptance.

In general, water, oil, saline, aqueous dextrose (glucose), polysorbate and related sugar solutions and glycols such as propylene glycol or polyethylene glycols are suitable carriers for parenteral solutions. Solutions or emulsions for parenteral administration preferably contain about 5–15% polysorbate 80 or lecithin, suitable stabilizing agents, and if necessary, buffer substances. Antioxidizing agents, such as but not limited to, sodium bisulfite, sodium sulfite, or ascorbic acid, either alone or combined, are suitable stabilizing agents. Also used are citric acid and its salts and sodium EDTA. In addition, parenteral solutions can contain preservatives, including but not limited to, benzalkonium chloride, methyl- or propyl-paraben, and chlorobutanol.

Suitable pharmaceutical carriers are further described in *Remington's Pharmaceutical Sciences*, 17th ed., Mack Publishing Company, Easton, Pa. (1990) a standard reference text in this field, which is incorporated herein by reference in its entirety.

Useful pharmaceutical dosage forms for administration of the compounds of this invention can be illustrated as follows:

5.3.1 Topical Formulation

For topical administration, butyric acid or butyric acid derivatives may be formulated as a solution, gel, lotion, ointment, cream, suspension, paste, liniment, powder, tincture, aerosol, transdermal drug delivery system, and the like in a pharmaceutically acceptable form by methods well known in the art. Actual methods for preparing topical formulations are known or apparent to those skilled in the art, and are described in detail in *Remington's Pharmaceutical Sciences*, 17th ed., Mack Publishing Company, Easton, Pa. (1990); and *Pharmaceutical Dosage Forms and Drug Delivery Systems*, 6th ed., Williams & Wilkins (1995).

In order to enhance the percutaneous absorption of the active ingredients, a number of agents may be added in the topical formulations, including, but not limited to, dimethylsulfoxide, dimethylacetamide, dimethylformamide, surfactants, azone, alcohol, acetone, propylene glycol and polyethylene glycol. In addition, physical methods may also be used to enhance transdermal penetration such as iontophoresis or sonophoresis.

The pharmaceutical compositions may be applied directly to the skin, such as the scalp. Alternatively, they may be delivered by various transdermal drug delivery systems, such as patches.

5.3.2 Capsules

A large number of unit capsules are prepared by filling standard two-piece hard gelatin capsules with the active ingredient and inactive ingredients such as lactose, cellulose and magnesium stearate. For example, a two-piece hard gelatin capsule may be filled with 10–500 milligrams of powdered active ingredient, 150 milligrams of lactose, 50 milligrams of cellulose, and 6 milligrams magnesium stearate.

5.3.3 Soft Gelatin Capsules

A mixture of active ingredients in ea digestible oil such as soybean oil, lecithin, cottonseed oil or olive oil is prepared and injected by means of a positive displacement pump into gelatin to form soft gelatin capsules containing 10–500 milligrams of the active ingredient. The capsules are washed and dried.

5.3.4 Tablets

A large number of tablets are prepared by conventional procedures to contain the active ingredient and inactive ingredients such as colloidal silicon dioxide, magnesium stearate, microcrystalline cellulose, starch and lactose. A tablet may be prepared so that the dosage unit is 10–500 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

6. EXAMPLE: BUTYRIC ACID DERIVATIVES PROTECT AGAINST CHEMOTHERAPY-INDUCED INJURY TO HAIR FOLLICLES

Certain butyric acid derivatives have been proposed as anti-cancer agents based on their ability to induce terminal differentiation of tumor cells. In order to determine whether such cell differentiation-inducing agents can induce maturation of non-malignant cells to result in a therapeutical effect, butylidene dibutyrate (see Section 5.2.1) and pivaloyloxymethyl butyrate (see Section 5.2.2) were tested in an animal model for their ability to protect against chemotherapy-induced injury to hair follicles.

6.1 Materials and Methods

6.1.1 Reagents

CY was manufactured by ASTA Medica AG, and purchased from Pharmacia Incorporated (Columbus, Ohio) labeled as "NEOSAR."

Butyric acid derivatives were prepared according to the methods disclosed in U.S. Pat. No. 5,200,553. In brief, butylidene dibutyrate was synthesized by reacting the anhydride of butyric acid with butyraldehyde in the presence of borontrifluoride diethyletherate, followed by washing and distillation to achieve purification. Pivaloyloxymethyl butyrate was synthesized by reacting butyric acid with chloromethylpivalate in the presence of triethylamine, followed by washing and distillation to achieve purification.

6.1.2 Animal Model

Normal C57BL6 mice were used for all experiments. In order to enhance the visibility of changes effected by treatment, wax depilation was performed on the back of each animal on day 0 (Paus et al., 1994, *Am. J. Pathol.* 144:719–734). A sufficient quantity of "surgi-wax" (manufactured by Ardell and purchased over the counter) was placed in a glass beaker and melted in a microwave. It was allowed to cool for a few minutes and applied over approximately 6 $cm^2$ of the dorsal fur of a mouse from the neck to behind the shoulders using a wooden applicator. The wax was allowed to harden for approximately two minutes, and then gently removed manually under traction, which also removed the entrapped hair. The process was repeated 2 to 3 times in order to produce a smooth, depilated area of relatively uniform size and shape (FIG. 1A and 1B).

The animals were then divided into different groups. A control group of animals received no further treatment. A separate group received a single dose of CY at 100 mg/kg of body weight intraperitoneally (i.p.) on day 9. A third group of animals received CY as described above and also received butylidene dibutyrate (about 950 mg/ml) topically at the site of hair depilation each day from day 6 to day 11. In the case of butylidene dibutyrate, 0.2 ml was administered three times per day on day 6 followed by 0.1 ml once a day from day 7 to 11. A fourth group of animals received CY as described above but also received pivaloyloxymethyl butyrate (about 970 mg/ml) topically at the site of hair depilation per day from day 6 to day 11. For pivaloyloxymethyl butyrate, 0.1 ml was administered once a day from day 6 to 11. Hair growth in all groups was monitored on days 7, 9, 14, 16, 20, 23, 27, 30 and 34. Hair growth was examined visually and histologically up to day 34.

6.2 Results

Hair regrowth in the control animals occurred rapidly and fully within 14 days of the pretreatment depilation (FIG. 2). When animals received a single dose of CY (100 mg/kg i.p.) nine days after depilation, hair growth was retarded for more than two weeks, such that complete regrowth was not achieved in the majority of the animals until day 30–34 (FIG. 3). However, when the CY-treated animals also received butylidene dibutyrate topically, hair regrowth was significantly accelerated as compared to the mice exposed to CY alone (FIG. 4).

Similarly, animals treated with pivaloyloxymethyl butyrate topically in combination with CY also exhibited accelerated regrowth of hair as compared to CY alone, although to a lesser degree than that achieved with butylidene dibutyrate treatment (FIG. 5). Histological examination of the follicles on day 14 confirmed the visual observations (FIG. 6A–6C).

These results show that administration of butyric acid derivatives protected animals against CY-induced injury to hair follicles, as evidenced by accelerated hair regrowth. Therefore, these compounds are particularly useful in protecting against injury to the hair follicles which results from certain clinical procedures, such as anesthesia, cancer chemotherapy or radiation therapy.

The present invention is not to be limited in scope by the exemplified embodiments, which are intended as illustrations of the invention. Indeed, various modifications of the invention in addition to those shown and described herein will become apparent to those skilled in the art from the foregoing description and accompanying drawings. Such modifications are also intended to fall within the scope of the appended claims.

The foregoing disclosure includes all the information deemed essential to enable those skilled in the art to practice the claimed invention. All publications cited herein are incorporated by reference in their entirety.

What is claimed is:

1. A method of protecting against injury to hair follicles in a subject, comprising:

administering to the subject an effective amount of a compound having the structure of:

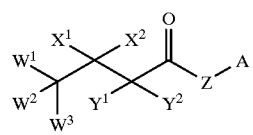

wherein:
$W^1$, $W^2$ and $W^3$ each independent from the other represents H, F, Br, Cl or I;
$X^1$ and $X^2$ each independent from the other represents H, F, Br, Cl, I, methyl, $CF_3$ ;
$Y^1$ and $Y^2$ each independent from the other represents H, F, Br, Cl, I, methyl, $CF_3$, ethyl or perfluoroethyl;
Z represents O; and
A represents or Q—$CHR^4$—O—C(=O)$R^5$ where Q represents a covalent bond or an alkyl; $R^4$ represents H or an alkyl; and $R^5$ represents alkyl or

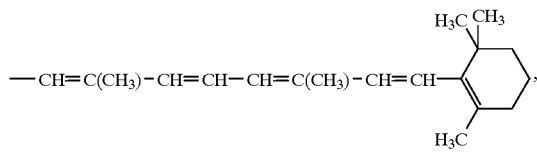

a pharmaceutically acceptable salt or prodrug thereof; and wherein said effective amount protects the subject against hair loss.

2. The method of claim 1 in which $W^2$, $W^3$, $X^2$ and $Y^2$ are H or F.

3. The method of claim 2 in which $W^1$ is H or F; $X^1$ is H, F, methyl, $CF_3$ and $Y^1$ is H, F, methyl, $CF_3$ ethyl or perfluoroethyl.

4. The method of claim 3 in which A is alkyl or Q—$CHR^4$—O—C(=O)$R^5$ where Q is a covalent bond or an alkyl; and $R^5$ is $C_1$-$C_7$ alkyl or

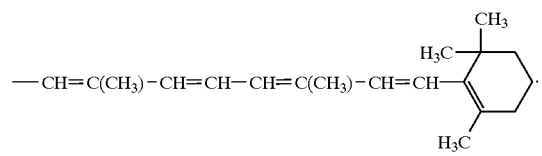

5. The method of claim 4 in which $W^1$ is H or F $X^1$ is H, F, methyl, $CF^3$; and $Y^1$ is H, F, methyl, $CF_3$, ethyl or perfluoroethyl.

6. The method of claim 5 in which A is alkyl or Q—$CHR^4$—O—C(=O)$R^5$ where Q is a covalent bond, $C_1$-$C_5$ alkyl or substituted alkyl where one or more substituents is —OC(=O)$CH_2CH_2CH_3$, $R^4$ is H or $C_1$-$C_5$ alkyl, and $R^5$ is $C_1$-$C_7$ alkyl or all trans

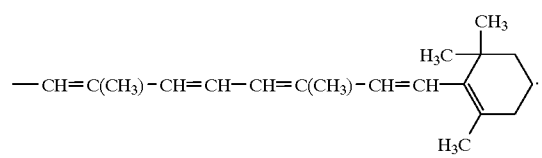

7. The method of claim 6 in which $W^1$, $W^2$, $W^3$, $X^1$, $X^2$, $Y^1$ and $Y^2$ are H.

8. The method of claim 1 in which A is Q—$CHR^4$—O—C(=O)$R^5$ where Q is a covalent bond.

9. The method of claim 1 in which A is $CHR^4$—O—C(=O)—$OR^5$.

10. The method of claim 1 in which the compound is pivaloyloxymethyl butyrate.

11. The method of claim 1 in which the compound is butylidene dibutyrate.

12. The method of claim 1 in which the compound is ethylidene dibutyrate.

13. The method of claim 1 in which the compound is 2,2-dimethylpropylidene dibutyrate.

14. The method of claim 1 in which the compound is methylidene dibutyrate.

15. The method of claim 1 in which the compound is (butyroyloxy)methyl octanoate.

16. The method of claim 1 in which the compound is ((2-methylpropanoyl)oxy)methyl butyrate.

17. The method of claim 1 in which the compound is retinoyloxymethyl butyrate.

18. The method of claim 1, wherein said subject is or has been exposed to chemotherapy.

* * * * *